United States Patent [19]
Maher et al.

[11] Patent Number: 5,925,754
[45] Date of Patent: Jul. 20, 1999

[54] EPSILON CAPROLACTAM COMPOSITIONS

[75] Inventors: John Michael Maher, Charleston; David Robert Bryant, South Charleston; Johnathan Eugene Holladay, Charleston; Thomas Carl Eisenschmid, Cross Lanes; John Robert Briggs, Charleston; Kurt Damar Olson, Cross Lanes, all of W. Va.

[73] Assignee: Union Carbide Chemicals & Plastics Technology Corporation, Danbury, Conn.

[21] Appl. No.: 08/956,745

[22] Filed: Oct. 23, 1997

Related U.S. Application Data

[63] Continuation-in-part of application No. 08/839,576, Apr. 15, 1997, and application No. 08/843,340, Apr. 15, 1997.

[51] Int. Cl.⁶ .................................................. C07D 223/10
[52] U.S. Cl. ............................................................... 540/485
[58] Field of Search ............................................. 540/485

[56] References Cited

U.S. PATENT DOCUMENTS

| | | | |
|---|---|---|---|
| 3,239,566 | 3/1966 | Slaugh et al. | 260/604 |
| 3,485,821 | 12/1969 | Sheehan | 260/239.3 |
| 3,652,549 | 3/1972 | Fujita et al. | 260/239.3 |
| 3,660,493 | 5/1972 | Johnson et al. | 260/604 |
| 3,947,503 | 3/1976 | Kummer | 260/635 |

(List continued on next page.)

FOREIGN PATENT DOCUMENTS

| | | |
|---|---|---|
| 0183545 | 6/1986 | European Pat. Off. . |
| 0271145 | 11/1987 | European Pat. Off. . |
| 0273489 | 6/1988 | European Pat. Off. . |
| 0343819 | 11/1989 | European Pat. Off. . |
| 0351616 | 1/1990 | European Pat. Off. . |
| 0405433 | 1/1990 | European Pat. Off. . |
| 0420510 | 3/1991 | European Pat. Off. . |
| 0448848 | 10/1991 | European Pat. Off. . |
| 0511126 | 4/1992 | European Pat. Off. . |
| 0556681 | 2/1993 | European Pat. Off. . |
| 0562450 | 3/1993 | European Pat. Off. . |
| 0577205 | 6/1993 | European Pat. Off. . |
| 0602442 | 6/1994 | European Pat. Off. . |
| 0643031 | 8/1994 | European Pat. Off. . |
| 0648731 | 4/1995 | European Pat. Off. . |
| 0662468 | 7/1995 | European Pat. Off. . |
| 0712828 | 11/1995 | European Pat. Off. . |
| 0738701 | 4/1996 | European Pat. Off. . |
| 0728732 | 8/1996 | European Pat. Off. . |
| 0729943 | 9/1996 | European Pat. Off. . |
| 0729944 | 9/1996 | European Pat. Off. . |
| 0761634 | 3/1997 | European Pat. Off. . |
| 6306012 | 4/1993 | Japan . |
| 1087510 | 1/1984 | Russian Federation . |
| 150453 | 9/1991 | Russian Federation . |
| 1254222 | 11/1971 | United Kingdom . |
| 1357735 | 6/1974 | United Kingdom . |
| 9426688 | 11/1994 | WIPO . |
| 9506025 | 3/1995 | WIPO . |
| 9506027 | 3/1995 | WIPO . |
| 9518089 | 7/1995 | WIPO . |
| 9518783 | 7/1995 | WIPO . |
| 9530680 | 11/1995 | WIPO . |

OTHER PUBLICATIONS

Van Leeuwen, P.W.N.M. et al., "The Hydroformylation of Butadiene Catalysed by Rhodium–Diphosphine Complexes." Journal of Molecular Catalysis (31), 1985, pp. 345–353.

Botteghi, Carlo et al., "Optically Active Aldehydes via Hydroformylation of 1,3–Dienes with Chiral Diphosphinerhodium Complexes." Journal of Organometallic Chemistry (184), 1980, pp. C17–C19.

Bertozzi, Sergio et al., "Selective Hydroformylation of Open–chain Conjugated Dienes Promoted by Mesitylene–solvated Rhodium Atoms to give B,y Unsaturated Monoaldehydes." Journal of Organometallic Chemistry (487), 1995, pp. 41–45.

Fell, Bernhard et al., "The Hydroformylation of Conjugated Dienes, V* Aliphatic Tertiary Phosphines and P–Substituted Phospholanes as Cocatalysts of the Rhodium–Catalysed Hydroformylation of 1,3–Dienes." Journal of Molecular Catalysis (2), 1977, pp. 211–218.

Bahrmann, H. et al., "The Hydroformylation of Conjugated Dienes Vi* Tertiary Aryl– and Arylalky–Phosphines as Ligands in the Rhodium Catalyzed Hydroformylation Reaction of Conjugated Dienes to Dialdehydes." Journal of Molecular Catalysis (8), 1980, pp. 329–337.

Fell, Bernhard et al., "Reaction Products of a Hydroformylation of Conjugated Dienes with Rhodium Carbonyl/tert–Phosphine Catalyst Systems." Chemical–Zeitung (99), 1975, pp. 1–19.

*Primary Examiner*—Richard L. Raymond
*Assistant Examiner*—Bruck Kifle
*Attorney, Agent, or Firm*—Gerald L. Coon

[57] ABSTRACT

This invention relates to a composition comprising (a) epsilon caprolactam and (b) one or more of 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-[3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide, 5-[4,5-di(4-hydroxybutyl)-2-pyridyl]pentanol, 4-[4,5-di(2-methoxypropyl)-2-pyridyl]-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1-pentanamine, 5-amino-2-methyl-1-pentanol, 5-imino-4-methyl-1-pentanamine and 2-butyl-4,5-dipropylpyridine, wherein the weight ratio of component (a) to component (b) is at least about 99 to 1. The epsilon caprolactam compositions are useful in the preparation of nylon 6.

9 Claims, No Drawings

U.S. PATENT DOCUMENTS

| | | | |
|---|---|---|---|
| 4,101,588 | 7/1978 | Nienburg et al. | 260/604 |
| 4,185,083 | 1/1980 | Carlock | 260/604 |
| 4,189,448 | 2/1980 | Carlock | 260/604 |
| 4,198,352 | 4/1980 | Kim et al. | 260/604 |
| 4,200,591 | 4/1980 | Hignett et al. | 260/604 |
| 4,200,592 | 4/1980 | Hignett et al. | 260/604 |
| 4,214,109 | 7/1980 | Carlock | 568/909 |
| 4,224,255 | 9/1980 | Smith | 568/451 |
| 4,263,449 | 4/1981 | Saito et al. | 560/263 |
| 4,376,212 | 3/1983 | Ohyama et al. | 560/205 |
| 4,409,418 | 10/1983 | Johnson et al. | 585/667 |
| 4,443,638 | 4/1984 | Yates | 568/882 |
| 4,447,661 | 5/1984 | Hoshiyama et al. | 586/882 |
| 4,451,679 | 5/1984 | Knifton et al. | 568/909 |
| 4,469,892 | 9/1984 | Knifton et al. | 568/454 |
| 4,482,749 | 11/1984 | Dennis et al. | 568/454 |
| 4,528,404 | 7/1985 | Oswald et al. | 568/454 |
| 4,550,195 | 10/1985 | Platz et al. | 560/206 |
| 4,567,306 | 1/1986 | Dennis et al | 568/455 |
| 4,586,987 | 5/1986 | Schneider et al. | 560/206 |
| 4,622,423 | 11/1986 | Burke | 562/522 |
| 4,625,068 | 11/1986 | Young | 568/454 |
| 4,647,707 | 3/1987 | van Vliet | 568/882 |
| 4,658,068 | 4/1987 | Henin | 568/451 |
| 4,730,040 | 3/1988 | Vagt et al. | 540/538 |
| 4,730,041 | 3/1988 | Hutmacher et al. | 540/538 |
| 4,731,445 | 3/1988 | Hutmacher et al. | 540/538 |
| 4,769,498 | 9/1988 | Billig et al. | 568/454 |
| 4,801,738 | 1/1989 | Schneider et al. | 560/177 |
| 4,824,817 | 4/1989 | Drent | 502/154 |
| 4,879,405 | 11/1989 | Naeumann et al. | 560/211 |
| 4,894,474 | 1/1990 | Maerkl et al. | 560/206 |
| 4,910,328 | 3/1990 | Bertleff et al. | 560/177 |
| 4,925,972 | 5/1990 | Maerkl et al. | 560/206 |
| 4,933,487 | 6/1990 | Hoelderich et al. | 560/205 |
| 5,003,102 | 3/1991 | Bertleff et al. | 560/177 |
| 5,026,901 | 6/1991 | D'Amore | 560/207 |
| 5,028,734 | 7/1991 | Drent | 560/207 |
| 5,041,642 | 8/1991 | Jenck | 562/522 |
| 5,068,398 | 11/1991 | Merger et al. | 560/156 |
| 5,145,995 | 9/1992 | Burke | 562/522 |
| 5,159,107 | 10/1992 | Panitz et al. | 560/206 |
| 5,177,228 | 1/1993 | Sato et al. | 554/129 |
| 5,198,577 | 3/1993 | Denis et al. | 562/522 |
| 5,250,726 | 10/1993 | Burke | 562/522 |
| 5,264,616 | 11/1993 | Roeper et al. | 560/175 |
| 5,288,903 | 2/1994 | Bunel et al. | 562/598 |
| 5,292,944 | 3/1994 | Atadan et al. | 562/590 |
| 5,306,848 | 4/1994 | Vargas | 568/883 |
| 5,312,979 | 5/1994 | Denis et al. | 562/522 |
| 5,312,996 | 5/1994 | Packett | 568/454 |
| 5,434,312 | 7/1995 | Fell et al. | 568/454 |
| 5,495,041 | 2/1996 | Sielcken et al. | 560/207 |
| 5,504,261 | 4/1996 | Mullin et al. | 568/862 |
| 5,583,250 | 12/1996 | Bahrmann et al. | 560/76 |

EPSILON CAPROLACTAM COMPOSITIONS

This application is a continuation-in-part of copending U.S. patent application Ser. Nos. 08/839,576 and 08/843,340, both filed Apr. 15, 1997.

BRIEF SUMMARY OF THE INVENTION

TECHNICAL FIELD

This invention relates to epsilon caprolactam compositions that are useful in the preparation of nylon 6.

BACKGROUND OF THE INVENTION

Epsilon caprolactam is a valuable intermediate that is useful, for example, in the production of nylon 6. Epsilon caprolactam currently used to produce nylon 6 contains various byproducts, e.g., cyclohexanol, cyclohexanone and 1-cyclohexanone oxime. A number of purification methods have been described in the art for the purpose of removing such byproducts from epsilon caprolactam. It would be desirable to obtain epsilon caprolactam free from such byproducts and thus eliminate the need to use the purification methods described in the art that are specific for removal of such byproducts.

DISCLOSURE OF THE INVENTION

The epsilon caprolactam compositions of this invention are distinctive insofar as they contain unique byproducts that result from reductive amination and cyclization of 6-carbon atom difunctional intermediates produced by carbonylation reactions utilizing butadiene as the initial feedstock. Certain of the byproducts have not before been disclosed in the art. The epsilon caprolactam compositions of this invention are further distinctive insofar as they are essentially free of byproducts that are produced by processes described in the art. The epsilon caprolactam compositions of this invention permit product separation with more stable intermediates and at more desirable points in a process thus allowing for improved efficiencies, and can eliminate the necessity for difficult separation steps that are used in prior art processes.

This invention relates to a composition comprising (a) epsilon caprolactam and (b) one or more of 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-[3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide, 5-[4,5-di(4-hydroxybutyl)-2-pyridyl]pentanol, 4-[4,5-di(2-methoxypropyl)-2-pyridyl-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1-pentanamine, 5-amino-2-methyl-1-pentanol, 5-imino-4-methyl-1-pentanamine and 2-butyl-4,5-dipropylpyridine, wherein the weight ratio of component (a) to component (b) is at least about 99 to 1.

This invention also relates to a composition comprising (a) epsilon caprolactam and (b) one or more of 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-(3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide and 2-butyl-4,5-dipropylpyridine, wherein the weight ratio of component (a) to component (b) is at least about 99 to 1.

This invention further relates to a composition comprising (a) epsilon caprolactam and (b) one or more of 5-[4,5-di(4-hydroxybutyl)-2-pyridyl]pentanol, 4-[4,5-di(2-methoxypropyl)-2-pyridyl]-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1-pentanamine, 5-amino-2-methyl-1-pentanol, 5-imino-4-methyl-1-pentanamine and 2-butyl-4,5-dipropylpyridine, wherein the weight ratio of component (a) to component (b) is at least about 99 to 1.

This invention yet further relates to compounds selected from the group consisting of 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-[3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide, 5-[4,5-di(4-hydroxybutyl)-2-pyridyl]pentanol, 4-[4,5-di(2-methoxypropyl)-2-pyridyl]-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1-pentanamine, 5-amino-2-methyl-1-pentanol, 5-imino-4-methyl-1-pentanamine and 2-butyl-4,5-dipropylpyridine.

DETAILED DESCRIPTION

The epsilon caprolactam compositions of this invention can be prepared by processes which selectively produce epsilon caprolactam and one or more of the following: 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-[3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide, 5-[4,5-di(4-hydroxybutyl)-2-pyridyl]pentanol, 4-[4,5-di(2-methoxypropyl)-2-pyridyl]-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1- pentanamine, 5-amino-2-methyl-1-pentanol, 5-imino-4-methyl-1-pentanamine and 2-butyl-4,5-dipropylpyridine. The epsilon caprolactam compositions of this invention are essentially free of byproducts that are produced by processes described in the art, e.g., cyclohexanol, cyclohexanone, 1-cyclohexanone oxime, 1-cyclohexanamine, phenol, aniline, nitrobenzene, p-toluidine, 1,2,3,4,5,6,7,8,9-octahydrophenazine, adiponitrile, aminocapronitrile, 1-methyl-2-azepanone, 6-(methylamino)hexanoic acid, 6-(methylamino)hexanamide, methyl formylvalerate ester, ethyl formylvalerate ester, propyl formylvalerate ester, methyl 6-aminohexanoate ester, ethyl 6-aminohexanoate ester, and propyl 6-aminohexanoate ester.

Preferred processes include pentenoic acid salt routes to epsilon caprolactam as described in copending U.S. patent application Ser. No. 08/839,576, supra, and pentenol routes to epsilon caprolactam as described in copending U.S. patent application Ser. No. 08/843,340, supra, the disclosures of which are incorporated herein by reference. The epsilon caprolactam compositions of this invention can be prepared without the need for separating less stable intermediates such as isomers of formylvaleric acids or salts or, isomers of hydroxyhexanal, and without the need for elaborate separation processes on less stable molecules. This allows for separation at more desirable points in an process for producing epsilon caprolactam thus allowing for improved efficiencies.

With respect to the pentenoic acid salt routes, the epsilon caprolactam compositions of this invention can be prepared by: (a) subjecting one or more substituted or unsubstituted alkadienes to hydroxycarbonylation in the presence of a hydroxycarbonylation catalyst and neutralization with ammonia to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or one or more substituted or unsubstituted epsilon caprolactam precursors to reductive cyclization in the presence of a reductive cyclization catalyst to produce said epsilon caprolactam composition.

Another pentenoic acid salt route to epsilon caprolactam involves: (a) subjecting one or more substituted or unsubstituted alkadienes to hydroxycarbonylation in the presence of a hydroxycarbonylation catalyst and neutralization with a base to produce one or more substituted or unsubstituted pentenoic acid salts; (b) subjecting said one or more substituted or unsubstituted pentenoic acid salts to hydroformylation in the presence of a hydroformylation catalyst to produce one or more substituted or unsubstituted formylvaleric acid salts and/or one or more substituted or unsubstituted epsilon caprolactam precursors; and (c) subjecting said one or more substituted or unsubstituted formylvaleric acid salts and/or said one or more substituted or unsubstituted epsilon caprolactam precursors to reductive amination in the presence of a reductive amination catalyst and cyclization optionally in the presence of a cyclization catalyst to produce said epsilon caprolactam composition.

The hydroxycarbonylation process involves converting one or more substituted or unsubstituted alkadienes, e.g., butadiene, to one or more substituted or unsubstituted unsaturated acids, e.g., cis-3-pentenoic acids, trans-3-pentenoic acids, 4-pentenoic acid, cis-2-pentenoic acids and/or trans-2-pentenoic acids, in one or more steps or stages. A preferred hydroxycarbonylation process useful in this invention is disclosed in U.S. patent application Ser. No. 08/839,578, filed Apr. 15, 1997, the disclosure of which is incorporated herein by reference.

Alkadienes useful in the hydroxycarbonylation are known materials and can be prepared by conventional processes. Reaction mixtures comprising alkadienes may be useful herein. The amounts of alkadienes employed in the hydroxycarbonylation is not narrowly critical and can be any amounts sufficient to produce unsaturated acids, preferably in high selectivities and acceptable rates. Alkadienes may be fed either batchwise or continuously.

The catalysts useful in the hydroxycarbonylation process include, for example, Group 8, 9 and 10 metals or metal complexes (supported or unsupported), Group 8, 9 and 10 metal halides and esters (e.g., $PdCl_2$ and $PdI_2$), palladium bis(dibenzylidene acetone), $Pd(OAc)_2$, palladium on carbon, dicarbonylacetylacetonato rhodium (I), $RhCl_3$, $Co_2(CO)_8$, Group 8, 9 and 10 metal-ligand complex catalysts and the like. The hydroxycarbonylation catalysts may be in homogeneous or heterogeneous form. Such catalysts may be prepared by methods known in the art.

The permissible metals which make up the metal-ligand complex catalysts include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being palladium, rhodium, cobalt, iridium and ruthenium, more preferably palladium, rhodium, cobalt and ruthenium, especially palladium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-, di-, tri- and poly-(organophosphites). Other permissible organophosphorus ligands include, for example, organophosphonites, organophosphinites, amino phosphines and the like. Other permissible ligands include, for example, heteroatom-containing ligands such as 2,2'-bipyridyl and the like. Still other permissible ligands include, for example, heteroatom-containing ligands such as described in U.S. patent application Ser. No. 08/818,781, filed Mar. 10, 1997, the disclosure of which is incorporated herein by reference. Mixtures of such ligands may be employed if desired in the metal-ligand complex catalyst and/or free ligand and such mixtures may be the same or different. By "free ligand" is meant ligand that is not complexed with (tied to or bound to) the metal, e.g., palladium atom, of the complex catalyst. This invention is not intended to be limited in any manner by the permissible ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

As indicated above, the hydroxycarbonylation is preferably carried out in the presence of a promoter. Suitable promoters include, for example, protonic organic acids, inorganic acids, Lewis acids, e.g., $BF_3$, and precursors capable of generating acids under hydroxycarbonylation conditions. The protonic organic acids are, for example, carboxylic acids and sulfonic acids with 1 to 30 carbon atoms. These carboxylic and sulfonic acids may be substituted with hydroxy, $C_1$–$C_4$ alkoxy, amine and halogenide groups, for example, chloride and bromide. Examples of preferred suitable carboxylic acids include benzoic acid or derived compounds, such as 2,4,6-trimethyl benzoic acid, meta- and parahydroxy benzoic acid, and product 3- and/or 4-pentenoic acids. Examples of preferred suitable sulfonic acids include methanesulfonic acid, trifluoromethanesulfonic acid and para-toluenesulfonic acid. Example inorganic acids include HCl, HBr, $HBF_4$, $H_3PO_4$, $H_3PO_3$, $H_2SO_4$ and HI. Examples of materials capable of generating acidic promoters under hydroxycarbonylation conditions include ammonium and alkyl ammonium halides, alkali metal halides, organic acyl halides, and organosilylhalides. The amount of promoter is generally in the range of from about 1 to 10 mole equivalents per metal, e.g., palladium.

The particular hydroxycarbonylation reaction conditions are not narrowly critical and can be any effective hydroxycarbonylation conditions sufficient to produce the unsaturated acids. The reactors may be stirred tanks, tubular reactors and the like. The exact reaction conditions will be governed by the best compromise between achieving high catalyst selectivity, activity, lifetime and ease of operability, as well as the intrinsic reactivity of the alkadienes in question and the stability of the alkadienes and the desired reaction product to the reaction conditions. Products may be recovered after a particular reaction zone and purified if desired although preferably they are introduced to the next reaction zone without purification. Recovery and purification may be by any appropriate means, which will largely be determined by the particular alkadiene and catalyst employed, and may include distillation, phase separation, extraction, absorption, crystallization, derivative formation and the like. Of course, it is to be understood that the hydroxycarbonylation reaction conditions employed will be governed by the type of unsaturated acid product desired.

The hydroxycarbonylation process may be conducted at a total gas pressure of carbon monoxide and alkadiene starting compound of from about 1 to about 10,000 psia. In general, the hydroxycarbonylation process is operated at a total gas pressure of carbon monoxide and alkadiene starting compound of less than about 3000 psia and more preferably less than about 2000 psia, the minimum total pressure being limited predominately by the amount of reactants necessary to obtain a desired rate of reaction. The total pressure of the hydroxycarbonylation process will be dependent on the particular catalyst system employed. It is understood that carbon monoxide can be employed alone, in mixture with other gases, e.g., hydrogen, or may be produced in situ under reaction conditions.

Further, the hydroxycarbonylation process may be conducted at a reaction temperature from about 25° C. to about 300° C. In general, a hydroxycarbonylation reaction temperature of about 50° C. to about 200° C. is preferred for all types of alkadiene starting materials. The temperature must be sufficient for reaction to occur (which may vary with catalyst system employed), but not so high that ligand or catalyst decomposition occurs. At high temperatures (which may vary with catalyst system employed), the formation of undesired byproducts, e.g., vinylcyclohexene, may occur.

The quantity of water used is not narrowly critical. The water:butadiene molar equivalents ratio is generally between about 0.1:1 and 100:1, preferably between about 0.1:1 and 10:1, and more preferably between about 0.5:1 and 2:1. Preferably the molar ratio of water:butadiene is about 1:1. Water may be fed either batchwise or continuously.

The substituted and unsubstituted unsaturated acids that can be prepared by the hydroxycarbonylation process include, for example, alkenoic acids such as cis-3-pentenoic acids, trans-3-pentenoic acids, 4-pentenoic acid, cis-2-pentenoic acids and/or trans-2-pentenoic acids and the like.

The neutralization process employed herein involves converting one or more substituted or unsubstituted unsaturated acids, e.g., pentenoic acids, to one or more substituted or unsubstituted unsaturated acid salts, e.g., pentenoic acid salts. It is understood that neutralization may be conducted during the hydroxycarbonylation stage or step.

In particular, one or more substituted or unsubstituted pentenoic acids can be reacted with a base to produce one or more substituted or unsubstituted pentenoic acid salts. For example, 3-pentenoic acid can be reacted with triethylamine to produce triethylammonium 3-pentenoate or with ammonia to produce ammonium 3-pentenoate. The neutralization of unsaturated acids to unsaturated acid salts may be carried out by conventional methods.

The base useful in the reaction of a pentenoic acid to a pentenoic acid salt is not narrowly critical. Illustrative bases include, for example, nitrogen containing bases (e.g., ammonia, trimethylamine, triethylamine, trioctylamine, ethyldioctylamine, tribenzylamine, diethylphenylamine, diphenylmethylamine, dimethylamine, diethanolamine, pyridine, bipyridine, benzimidazole, benzotriazole, ethylenediamine, and tetramethylethylenediamine), alkali metal hydroxides, alkoxides, carboxylates, carbonates and phosphates (e.g., sodium hydroxide, potassium hydroxide, lithium hydroxide, sodium methoxide, lithium butoxide, sodium carbonate, and potassium phosphate), ammonium or alkyl ammonium hydroxides and carboxylates (e.g. ammonium hydroxide, trimethylbutylammonium hydroxide, tetrabutylammonium hydroxide, trimethylbenzylammonium hydroxide, triethylphenylammonium acetate, and tetraethylammonium benzoate) alkyl phosphonium hydroxides and carboxylates, (e.g. octyltrimethylphosphonium hydroxide, tetrabutylphosponium hydroxide, ethyltriphenylphosphonium hydroxide, trimethylbenzylphosponium hydroxide), bis(hydrocarbyl-phosphine)iminium hydroxides, (e.g., bis (triphenylphosphine)iminium hydroxide, bis (tribenzylphosphine)iminium hydroxide). Alternatively, the base used for neutralization of the pentenoic acid may be incorporated into the ligand structure (e.g. tris (dimethylaminophenyl)-phosphine, bis (dimethylaminoethyl)phenylphosphine), either as the metal-ligand complex catalyst or as free ligand. The amount of base employed should be sufficient to neutralize, at least in part, the unsaturated acids.

The reactors and reaction conditions for the neutralization reaction steps are known in the art. The particular neutralization reaction conditions are not narrowly critical and can be any effective neutralization conditions sufficient to produce one or more unsaturated acid salts. The reactors may be stirred tanks, tubular reactors and the like. The exact reaction conditions will be governed by the best compromise between achieving high selectivity and ease of operability, as well as the intrinsic reactivity of the starting materials in question and the stability of the starting materials and the desired reaction product to the reaction conditions. Recovery and purification may be by any appropriate means, and may include distillation, phase separation, extraction, absorption, crystallization, derivative formation and the like.

The particular neutralization reaction conditions are not narrowly critical and can be any effective neutralization procedures sufficient to produce one or more unsaturated acid salts. For the reaction of unsaturated acids with a base, the temperature must be sufficient for reaction to occur but not so high that the unsaturated acids undergo undesirable side reactions, i.e., a temperature of from about 0° C. to about 200° C., preferably about 20° C. to about 100° C.

Illustrative substituted and unsubstituted unsaturated acid salts that can be prepared by the neutralization processes include one or more of the following: alkenoic acid salts such as triethylammonium 3-pentenoate, ammonium 3-pentenoate, octyltriethylammonium 3-pentenoate, including mixtures comprising one or more unsaturated acid salts.

The hydroformylation stage or step involves the production of aldehyde acid salts, e.g., formylvaleric acid salts, and/or one or more substituted or unsubstituted epsilon caprolactam precursors by reacting an olefinic compound salt, e.g., pentenoic acid salt, with carbon monoxide and hydrogen in the presence of a solubilized metal-ligand complex catalyst and free ligand in a liquid medium that also contains a solvent for the catalyst and ligand. The processes may be carried out in a continuous single pass mode in a continuous gas recycle manner or more preferably in a continuous liquid catalyst recycle manner as described below. The hydroformylation processing techniques employable herein may correspond to any known processing techniques such as preferably employed in conventional liquid catalyst recycle hydroformylation reactions. As used herein, substituted or unsubstituted epsilon caprolactam precursors is contemplated to include, but are not limited to, one or more formylvaleric acid salts, iminocaproic acid and/or salts thereof, aminocaproic acid and/or salts thereof, caprolactam, caprolactone, imines, hemiaminals, aminals, imides, amides or amines derived from formylvaleric acid and its salts, and the corresponding dimers, trimers and oligomers of any of the above species.

The catalysts useful in the hydroformylation stage or step include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-, di-, tri- and poly-(organophosphites). Other permissible organophosphorus ligands include, for example, organophosphonites, organophosphinites, amino phosphines and the like. Still other permissible ligands include, for example, heteroatom-containing ligands such as described in U.S. patent application Ser. No. 08/818,781, supra. Mixtures of such ligands may be employed if desired in the metal-ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

As noted the hydroformylation reactions involve the use of a metal-ligand complex catalyst as described herein. Of course mixtures of such catalysts can also be employed if desired. The amount of metal-ligand complex catalyst present in the reaction medium of a given hydroformylation reaction need only be that minimum amount necessary to provide the given metal concentration desired to be employed and which will furnish the basis for at least the catalytic amount of metal necessary to catalyze the particular hydroformylation reaction involved such as disclosed e.g. in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydroformylation reaction conditions and solvent employed.

In general, the organophosphorus ligand concentration in hydroformylation reaction mixtures may range from between about 0.005 and 25 weight percent based on the total weight of the reaction mixture. Preferably the ligand concentration is between 0.01 and 15 weight percent, and more preferably is between about 0.05 and 10 weight percent on that basis.

In general, the concentration of the metal in the hydroformylation reaction mixtures may be as high as about 2000 parts per million by weight or greater based on the weight of the reaction mixture. Preferably the metal concentration is between about 50 and 1000 parts per million by weight based on the weight of the reaction mixture, and more preferably is between about 70 and 800 parts per million by weight based on the weight of the reaction mixture.

In addition to the metal-ligand complex catalyst, free ligand (i.e., ligand that is not complexed with the metal) may also be present in the hydroformylation reaction medium. The free ligand may correspond to any of the above-defined ligands discussed above as employable herein. It is preferred that the free ligand be the same as the ligand of the metal-ligand complex catalyst employed. However, such ligands need not be the same in any given process. The hydroformylation reaction may involve up to 100 moles, or higher, of free ligand per mole of metal in the hydroformylation reaction medium. Preferably the hydroformylation reaction is carried out in the presence of from about 0.25 to about 50 moles of coordinatable phosphorus, and more preferably from about 0.5 to about 30 moles of coordinatable phosphorus per mole of metal present in the reaction medium; said amounts of coordinatable phosphorus being the sum of both the amount of coordinatable phosphorus that is bound (complexed) to the metal present and the amount of free (non-complexed) coordinatable phosphorus present. Of course, if desired, make-up or additional coordinatable phosphorus can be supplied to the reaction medium of the hydroformylation reaction at any time and in any suitable manner, e.g. to maintain a predetermined level of free ligand in the reaction medium.

The hydroformylation reaction conditions may include any suitable type hydroformylation conditions heretofore employed for producing aldehydes. For instance, the total gas pressure of hydrogen, carbon monoxide and other components of the hydroformylation process may range from about 1 to about 10,000 psia. In general, the hydroformylation process is operated at a total gas pressure of hydrogen, carbon monoxide and all other components of less than about 1500 psia and more preferably less than about 1000 psia, the minimum total pressure being limited predominately by the amount of reactants necessary to obtain a desired rate of reaction. The total pressure employed in the hydroformylation reaction may range in general from about 20 to about 3000 psia, preferably from about 50 to 2000 psia and more preferably from about 75 to about 1000 psia. The total pressure of the hydroformylation process will be dependent on the particular catalyst system employed.

More specifically, the carbon monoxide partial pressure of the hydroformylation reaction in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed.

Further, the hydroformylation process may be conducted at a reaction temperature from about 20° C. to about 200° C., preferably from about 50° C. to about 150° C., and more preferably from about 65° C. to about 115° C. The temperature must be sufficient for reaction to occur (which may vary with catalyst system employed), but not so high that ligand or catalyst decomposition occurs. At high temperatures (which may vary with catalyst system employed), isomerization of intermediates to undesired isomers may occur.

Of course, it is to be also understood that the hydroformylation reaction conditions employed will be governed by the type of aldehyde salt product desired.

Illustrative substituted and unsubstituted aldehyde acid salt intermediates that can be prepared by the processes of this invention include substituted and unsubstituted formylcarboxylic acid salts such as 5-formylvaleric acid salts and the like, e.g., triethylammonium 5-formylvalerate, ammonium 5-formylvalerate and octyltriethylammonium 5-formylvalerate.

Illustrative substituted and unsubstituted epsilon caprolactam precursors that can be prepared by the processes of this invention include one or more substituted and unsubstituted 5-formylvaleric acid salts, iminocaproic acid and/or salts thereof, aminocaproic acid and/or salts thereof, caprolactam, caprolactone, imines, hemiaminals, aminals, imides, amides or amines derived from formylvaleric acid and its salts, and the corresponding dimers, trimers and oligomers of any of the above species.

The reductive cyclization process involves converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams in one or more steps or stages.

The particular reductive cyclization reaction conditions are not narrowly critical and can be any effective hydrogenation and cyclization conditions sufficient to produce the epsilon caprolactams. The reactors may be stirred tanks, tubular reactors and the like. The exact reaction conditions will be governed by the best compromise between achieving high catalyst selectivity, activity, lifetime and ease of operability, as well as the intrinsic reactivity of the formylvaleric acid salts and/or epsilon caprolactam precursors in question and the stability of the formylvaleric acid salts and/or epsilon caprolactam precursors and the desired reaction product to the reaction conditions. Illustrative of certain reaction conditions that may be employed in the hydrogenation and/or cyclization processes are described, for example, in U.S. Pat. Nos. 3,652,549 and 4,730,041, the disclosures of which are incorporated herein by reference. Products may be recovered after a particular reaction zone and purified if desired although they may be introduced to the next reaction zone without purification. Recovery and purification may be by any appropriate means, which will largely be determined by the particular epsilon caprolactam precursor employed, and may include distillation, phase separation, extraction, absorption, crystallization, derivative formation and the like.

The hydrogenation may be carried out using a variety of known catalysts in conventional amounts. Such catalysts comprise a variety of materials, including homogeneous and heterogeneous catalysts, such as palladium, ruthenium, platinum, rhodium, copper chromite, nickel, copper, cobalt, and the like. These metal catalysts can be supported on a variety of supports, including titania, magnesium silicate, alumina, vanadia and the like, and may be further promoted by additional metals or other additives, for example, barium, manganese, zirconium, selenium, calcium, molybdenum, cobalt, and the like. Other illustrative catalysts comprise a variety of materials, including homogeneous and heterogeneous catalysts, or other Group 8, 9 and 10 metals, copper, chromium oxide, and a variety of metal nitrides and carbides, and the like. These metal catalysts can be supported on a variety of supports, including titania, lanthanum oxide, ceria, silicon carbide, magnesium silicate, aluminas, silica-aluminas, vanadia and the like, and may be further promoted by additional metals or other additives, for example, barium, manganese, zirconium, selenium, calcium, molybdenum, cobalt or other Group 8, 9 and 10 metals, copper, iron, and zinc. A variety of homogeneous catalysts may also be employed, for example rhodium, ruthenium, cobalt, nickel and the like. Such catalysts can be promoted or stabilized by a variety of ligands including nitrogen or phosphorus containing materials such amines, phosphines, phosphites and similar materials.

The hydrogenation reaction may be carried out in any desired manner, for example in a tubular or a stirred tank reactor, and the like. The hydrogenation reaction can be carried out by conventional methods. For example, reaction temperatures may range from about 50° C. to about 400° C. or higher, preferably from about 100° C. to about 300° C. for a period of about 1 hour or less to about 4 hours or longer with the longer time being used at the lower temperature. Reaction pressures may range from atmospheric or subatmospheric to about 3000 psi or greater. Preferably, mild temperatures and low pressures are generally considered desirable, consistent with acceptable catalyst performance and lifetime, and epsilon caprolactam precursor and epsilon caprolactam product stability. The amount of hydrogenation catalyst used is dependent on the particular hydrogenation catalyst employed and can range from about 0.01 weight percent or less to about 10 weight percent or greater of the total weight of the starting materials.

The cyclization reaction of an epsilon caprolactam precursor in which at least one functionality is a nitrogen containing functional group such as amine may or may not need a catalyst, depending on the particular epsilon caprolactam precursor employed. Although it may not be absolutely necessary to employ a catalyst, it still may be desirable to do so to improve the selectivity or rate of the transformation. Other epsilon caprolactam precursors may necessitate the use of an appropriate catalyst. Since the mechanism of the cyclization reaction depends on the epsilon caprolactam precursor, the useful catalysts will be selected based upon the epsilon caprolactam precursor employed.

A two phase system may also be used, providing adequate mixing is achieved. Such a system, however, may be used to facilitate recovery of epsilon caprolactam after the cyclization reaction by extraction, phase separation or crystallization. Cyclization reaction conditions may range from about 0° C. to about 400° C. and subatmospheric to about 3000 psi or greater for a period of about 1 hour or less to about 4 hours or longer with the longer time being used at the lower temperature, more preferably from about 50° C. to about 350° C. and from about 50 psi to about 2500 psi. The amount of catalyst used, if any, is dependent on the particular catalyst employed and can range from about 0.01 weight percent or less to about 10 weight percent or greater of the total weight of the starting materials. It may be desirable to combine hydrogenation and cyclization steps into a single reaction zone.

The reductive amination and cyclization process involves converting one or more substituted or unsubstituted formylvaleric acid salts, e.g., 5-formylvaleric acid salt, and/or one or more substituted or unsubstituted epsilon caprolactam precursors to one or more substituted or unsubstituted epsilon caprolactams in one or more steps or stages.

The particular amination and cyclization reaction conditions are not narrowly critical and can be any effective amination and cyclization conditions sufficient to produce the epsilon caprolactam. The reactors may be stirred tanks, tubular reactors and the like. The exact reaction conditions will be governed by the best compromise between achieving high catalyst selectivity, activity, lifetime and ease of operability, as well as the intrinsic reactivity of the formylvaleric acid salts and/or epsilon caprolactam precursors in question and the stability of the formylvaleric acid salts and/or epsilon caprolactam precursors and the desired reaction product to the reaction conditions. Illustrative of certain reaction conditions that may be employed in the reductive amination and/or cyclization processes are described, for example, in U.S. Pat. Nos. 4,730,840, 4,730,841, 4,731,445 and 5,068,398, the disclosures of which are incorporated herein by reference. Products may be recovered after a particular reaction zone and purified if desired although they may be introduced to the next reaction zone without purification. Recovery and purification may be by any appropriate means, which will largely be determined by the particular epsilon caprolactam precursor employed, and may include distillation, phase separation, extraction, absorption, crystallization, derivative formation and the like.

The reductive amination reaction can be conducted at a temperature of from about 0° C. to about 200° C. for a period of about 1 hour or less to about 4 hours or longer with the longer time being used at the lower temperature, preferably from about 10° C. to about 150° C. for about 1 hour or less to about 2 hours or longer, and more preferably at about 20° C. to about 125° C. for about 1 hour or less. The temperature should be sufficient for reaction to occur (which may vary with catalyst system) but not so high as to cause 5-formylvaleric acid salt decomposition or polymerization.

The reductive amination reaction can be conducted over a wide range of pressures ranging from about 20 psig to about 2000 psig. It is preferable to conduct the reductive amination reaction at pressures of from about 100 psig to about 1000 psig. The reductive amination reaction is preferably effected in the liquid or vapor states or mixtures thereof. The total pressure will depend on the catalyst system used. Hydrogen partial pressure can be chosen to maximize the lifetime of the hydrogenation catalyst.

Ammonia is preferably employed as the aminating agent in these reactions in conventional amounts, preferably in excess amounts, and it may be fed to the reactor in a variety of ways, including as a liquid, and a gas, in solution in for example water, or as ammonium salts in solution or in some other appropriate manner. Any excess ammonia is preferably separated off after amination is completed. The formylvaleric acid salts and/or epsilon caprolactam precursors may be fed to the reactor in any convenient manner, such as in solution, or as a neat liquid.

Some of the reaction steps or stages may involve the use of a catalyst. Such catalysts are known in the art and can be used in conventional amounts. For example, the hydrogenation of an imine to an amine may advantageously employ an appropriate hydrogenation catalyst.

Catalysts suitable for possible intermediate imination reactions, e.g., conversion of an aldehyde to an imine, include mild acids, for example mineral acids, and carboxylic acids, such as hydrochloric acid, phosphoric acid, sulfuric acid, acetic acid benzoic acid, and the like. Other acidic materials may also be used, such as molecular sieves, silicas, aluminas and aluminosilicas, clays, and hydrous titanates. Heteropolyacids, sulfonic acids, phenols or other mildly acidic materials may also be used.

A further transformation in the reaction sequence is the reduction of imine to amine functionality, i.e., hydrogenation reaction. This transformation may be carried out using a variety of known catalysts, such as hydrogenation or dehydrogenation catalysts, in conventional amounts. Such catalysts comprise a variety of materials, including homogeneous and heterogeneous catalysts, such as palladium, ruthenium, platinum, rhodium, copper chromite, nickel, copper, cobalt, and the like. These metal catalysts can be supported on a variety of supports, including titania, magnesium silicate, alumina, vanadia and the like, and may be further promoted by additional metals or other additives, for example, barium, manganese, zirconium, selenium, calcium, molybdenum, cobalt, and the like. Other illustrative catalysts comprise a variety of materials, including homogeneous and heterogeneous catalysts, or other Group 8, 9 and 10 metals, copper, chromium oxide, and a variety of metal nitrides and carbides, and the like. These metal catalysts can be supported on a variety of supports, including titania, lanthanum oxide, ceria, silicon carbide, magnesium silicate, aluminas, silica-aluminas, vanadia and the like, and may be further promoted by additional metals or other additives, for example, barium, manganese, zirconium, selenium, calcium, molybdenum, cobalt or other Group 8, 9 and 10 metals, copper, iron, and zinc. A variety of homogeneous catalysts may also be employed, for example rhodium, ruthenium, cobalt, nickel and the like. Such catalysts can be promoted or stabilized by a variety of ligands including nitrogen or phosphorus containing materials such amines, phosphines, phosphites and similar materials.

The hydrogenation reaction may be carried out in any desired manner, for example in a tubular or a stirred tank reactor, and the like. The hydrogenation reaction can be carried out by conventional methods. For example, reaction temperatures may range from about 50° C. to about 400° C. or higher, preferably from about 100° C. to about 300° C. for a period of about 1 hour or less to about 4 hours or longer with the longer time being used at the lower temperature.

Reaction pressures may range from atmospheric or subatmospheric to about 3000 psi or greater. Preferably, mild temperatures and low pressures are generally considered desirable, consistent with acceptable catalyst performance and lifetime, and epsilon caprolactam precursor and epsilon caprolactam product stability. The amount of hydrogenation catalyst used is dependent on the particular hydrogenation catalyst employed and can range from about 0.01 weight percent or less to about 10 weight percent or greater of the total weight of the starting materials.

The cyclization reaction of an epsilon caprolactam precursor in which at least one functionality is a nitrogen containing functional group such as amine or imine may or may not need a catalyst, depending on the particular epsilon caprolactam precursor employed. Although it may not be absolutely necessary to employ a catalyst, it still may be desirable to do so to improve the selectivity or rate of the transformation. Other epsilon caprolactam precursors may necessitate the use of an appropriate catalyst. Since the mechanism of the cyclization reaction depends on the epsilon caprolactam precursor, the useful catalysts will be selected based upon the epsilon caprolactam precursor employed.

A two phase system may also be used, providing adequate mixing is achieved. Such a system, however, may be used to facilitate recovery of epsilon caprolactam after the cyclization reaction by extraction, phase separation or crystallization. Cyclization reaction conditions may range from about 0° C. to about 400° C. and subatmospheric to about 3000 psi or greater for a period of about 1 hour or less to about 4 hours or longer with the longer time being used at the lower temperature, more preferably from about 50° C. to about 350° C. and from about 50 psi to about 2500 psi. The amount of catalyst used, if any, is dependent on the particular catalyst employed and can range from about 0.01 weight percent or less to about 10 weight percent or greater of the total weight of the starting materials. It may be desirable to combine amination and cyclization steps into a single reaction zone.

The epsilon caprolactam compositions of this invention prepared by the pentenoic acid salt routes comprise epsilon caprolactam and certain byproducts unique to the processes. Illustrative of such byproducts include, for example, one or more of those selected from the group consisting of 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-[3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide and 2-butyl-4,5-dipropylpyridine. These byproducts will typically be present in the final purification steps of the pentenoic acid salt routes. Other byproducts that will typically be present in the final purification steps of the pentenoic acid salt routes include, for example, one or more of those selected from the group consisting of 5-methyl-2-piperidinone, 4-ethyl-2-pyrrolidinone, 2-butyl-3,5-diisopropylpyridine, 6-aminohexanoic acid or salt or amide, 5-amino-4-methylpentanoic acid or salt or amide, and 4-amino-3-ethylbutanoic acid or salt or amide. Byproducts that typically will be separated before the final purification steps include, for example, one or more of those selected from the group consisting of 5-formylvaleric acid, 4-formylvaleric acid, 3-formylvaleric acid, 6-hydroxyhexanoic acid, 5-hydroxy-4-methylpentanoic acid, 3-ethyl-4-hydroxybutanoic acid, 1,3,7-octatriene, 2,7-nonanoic acid, adipic acid, 3-pentenoic acid and pentanoic acid.

Other byproducts that will typically be present in the epsilon caprolactam compositions derived from the pentenoic acid salt routes include, for example, one or more of those selected from the group consisting of 5-oxo-4-methylpentanoic acid or salt or amide, 5-imino-4-methylpentanoic acid or salt or amide, 5-amino-4-methylpentanoic acid or salt or amide, 5-methyl-2-piperidinone, 4-oxo-3-ethylbutanoic acid or salt or amide, 4-imino-3-ethylbutanoic acid or salt or amide, 4-amino-3-ethylbutanoic acid or salt or amide and 4-ethyl-2-pyrrolidinone.

An illustrative byproduct is represented by the formula:

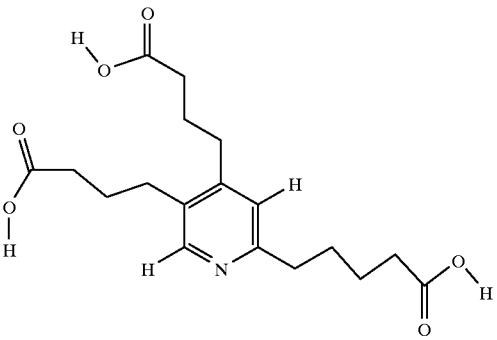

5-[4,5-di(3-carboxypropyl)-2-pyridyl]pentanoic acid or salt or amide.

Of course it is recognized that byproducts incorporating substituted or unsubstituted linear, branched and/or linear and branched isomers, e.g., pyridines, are included within the scope of this invention.

The amount of epsilon caprolactam and byproducts present in the compositions of this invention can vary over a wide range. Preferably, the weight ratio of epsilon caprolactam to byproducts is at least about 90 to 10, more preferably at least about 99 to 1, and most preferably at least about 99.9 to 0.1.

With respect to the pentenol routes, the epsilon caprolactam compositions of this invention can be prepared by: (a) subjecting one or more substituted or unsubstituted alkadienes, e.g., butadiene, to hydrocarbonylation in the presence of a hydrocarbonylation catalyst, e.g., a metal-organophosphorus ligand complex catalyst, to produce one or more substituted or unsubstituted unsaturated alcohols; (b) subjecting said one or more substituted or unsubstituted unsaturated alcohols to hydroformylation in the presence of a hydroformylation catalyst, e.g., a metal-organophosphorus ligand complex catalyst, to produce one or more substituted or unsubstituted hydroxyaldehydes; and (c) subjecting said one or more substituted or unsubstituted hydroxyaldehydes to amination/hydrogenation and dehydrogenation/cyclization to produce said epsilon caprolactam composition. Such a process is disclosed in copending U.S. application Ser. No. 08/843,340, supra.

The hydrocarbonylation stage or step involves converting one or more substituted or unsubstituted alkadienes to one or more substituted or unsubstituted unsaturated alcohols and/or converting one or more substituted or unsubstituted pentenals to one or more substituted or unsubstituted hydroxyaldehydes. The hydrocarbonylation may be conducted in one or more steps or stages, preferably a one step process. A preferred hydrocarbonylation process useful in this invention is disclosed in U.S. patent application Ser. No. 08/843,381, filed Apr. 15, 1997, the disclosure of which is incorporated herein by reference.

The hydrocarbonylation stage or step involves the production of unsaturated alcohols or hydroxyaldehydes by reacting an alkadiene or pentenals with carbon monoxide and hydrogen in the presence of a metal-ligand complex catalyst and optionally free ligand in a liquid medium that also contains a promoter. The reaction may be carried out in a continuous single pass mode in a continuous gas recycle manner or more preferably in a continuous liquid catalyst recycle manner as described below. The hydrocarbonylation processing techniques employable herein may correspond to any known processing techniques.

The catalysts useful in the hydrocarbonylation stage or step include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-organophosphorus ligand complexes and free organophosphorus ligand include mono-, di-, tri- and higher poly-(organophosphorus) compounds, preferably those of high basicity and low steric bulk. Illustrative permissible organophosphorus ligands include, for example, organophosphines, organophosphites, organophosphonites, organophosphinites, organophosphorus nitrogen-containing ligands, organophosphorus sulfur-containing ligands, organophosphorus silicon-containing ligands and the like. Other permissible ligands include, for example, heteroatom-containing ligands such as described in U.S. patent application Ser. No. 08/818,781, supra. Mixtures of such ligands may be employed if desired in the metal-ligand complex catalyst and/or free ligand and such mixtures may be the same or different. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

As noted the hydrocarbonylation stage or step involves the use of a metal-ligand complex catalyst as described herein. Of course mixtures of such catalysts can also be employed if desired. The amount of metal-ligand complex catalyst present in the reaction medium of a given hydrocarbonylation process need only be that minimum amount necessary to provide the given metal concentration desired to be employed and which will furnish the basis for at least the catalytic amount of metal necessary to catalyze the particular hydrocarbonylation process involved such as disclosed, for example, in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydrocarbonylation process conditions and solvent employed.

The particular hydrocarbonylation reaction conditions are not narrowly critical and can be any effective hydrocarbonylation procedures sufficient to produce one or more unsaturated alcohols or hydroxyaldehydes. The exact reaction conditions will be governed by the best compromise between achieving high catalyst selectivity, activity, lifetime and ease of operability, as well as the intrinsic reactivity of the starting materials in question and the stability of the starting materials and the desired reaction product to the reaction conditions. The hydrocarbonylation stage or step conditions may include any suitable type hydrocarbonylation conditions heretofore employed for producing alcohols or hydroxyaldehydes. The total pressure employed in the hydrocarbonylation process may range in general from about 1 to about 10,000 psia, preferably from about 20 to 3000 psia and more preferably from about 50 to about 2000 psia. The total pressure of the hydrocarbonylation process will be dependent on the particular catalyst system employed.

More specifically, the carbon monoxide partial pressure of the hydrocarbonylation process in general may range from about 1 to about 3000 psia, and preferably from about 3 to about 1500 psia, while the hydrogen partial pressure in general may range from about 1 to about 3000 psia, and preferably from about 3 to about 1500 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. The carbon monoxide and hydrogen partial pressures will be dependent in part on the particular catalyst system employed. It is understood that carbon monoxide and hydrogen can be employed separately, either alone or in mixture with each other, i.e., synthesis gas, or may be produced in situ under reaction conditions and/or be derived from the promoter or solvent (not necessarily involving free hydrogen or carbon monoxide). In an embodiment, the hydrogen partial pressure and carbon monoxide partial pressure are sufficient to prevent or minimize derivatization, e.g., hydrogenation of penten-1-ols or further hydrocarbonylation of penten-1-ols or hydrogenation of alkadienes. The hydrocarbonylation is preferably conducted at a hydrogen partial pressure and carbon monoxide partial pressure sufficient to prevent or minimize formation of substituted or unsubstituted pentan-1-ols, and/or substituted or unsubstituted valeraldehydes.

Further, the hydrocarbonylation process may be conducted at a reaction temperature from about 20° C. to about 200° C., preferably from about 50° C. to about 150° C., and more preferably from about 65° C. to about 115° C. The temperature must be sufficient for reaction to occur (which may vary with catalyst system employed), but not so high that ligand or catalyst decomposition occurs. At high temperatures (which may vary with catalyst system employed), conversion of penten-1-ols to undesired byproducts may occur.

The hydrocarbonylation process is also conducted in the presence of a promoter. As used herein, "promoter" means an organic or inorganic compound with an ionizable hydrogen of pKa of from about 1 to about 35. Illustrative promoters include, for example, protic solvents, organic and inorganic acids, alcohols, water, phenols, thiols, thiophenols, nitroalkanes, ketones, nitriles, amines (e.g., pyrroles and diphenylamine), amides (e.g., acetamide), mono-, di- and trialkylammonium salts, and the like.

Approximate pKa values for illustrative promoters useful in this invention are given in the Table II below. The promoter may be present in the hydrocarbonylation reaction mixture either alone or incorporated into the ligand structure, either as the metal-ligand complex catalyst or as free ligand, or into the alkadiene structure. The desired promoter will depend on the nature of the ligands and metal of the metal-ligand complex catalysts. In general, a catalyst with a more basic metal-bound acyl or other intermediate will require a lower concentration and/or a less acidic promoter.

The concentration of the promoter employed will depend upon the details of the catalyst system employed. Without wishing to be bound by theory, the promoter component must be sufficiently acidic and in sufficient concentration to transfer a hydrogen ion to or otherwise activate the catalyst-bound acyl or other intermediate. It is believed that a promoter component acidity or concentration which is insufficient to transfer a hydrogen ion to or otherwise activate the catalyst-bound acyl or other intermediate will result in the formation of pentenal products, rather than the preferred penten-1-ol products. The ability of a promoter component to transfer a hydrogen ion to or otherwise activate the catalyst-bound acyl or other intermediate may be governed by several factors, for example, the concentration of the promoter component, the intrinsic acidity of the promoter component (the pKa), the composition of the reaction medium (e.g., the reaction solvent) and the temperature. Promoters are chosen on the basis of their ability to transfer a hydrogen ion to or otherwise activate such a catalyst-bound acyl or other intermediate under reaction conditions sufficient to result in the formation of alcohol or hydroxyaldehyde products, but not so high as to result in detrimental side reactions of the catalyst, reactants or products. In cases where the promoter component acidity or concentration is insufficient to do so, aldehyde products (e.g., pentenals) are initially formed which may or may not be subsequently converted to unsaturated alcohols, e.g., penten-1-ols, or hydroxyaldehydes, e.g., 6-hydroxyhexanal.

Depending on the particular catalyst and reactants employed, suitable promoters preferably include solvents, for example, alcohols (e.g., the unsaturated alcohol or hydroxyaldehyde products such as penten-1-ols or 6-hydroxyhexanals), thiols, thiophenols, selenols, tellurols, alkenes, alkynes, aldehydes, higher boiling byproducts, ketones, esters, amides, primary and secondary amines, alkylaromatics and the like. Any suitable promoter which does not unduly adversely interfere with the intended hydrocarbonylation process can be employed. Permissible protic solvents have a pKa of about 1–35, preferably a pKa of about 3–30, and more preferably a pKa of about 5–25. Mixtures of one or more different solvents may be employed if desired.

In general, with regard to the production of unsaturated alcohols or hydroxyaldehydes, it is preferred to employ unsaturated alcohol or hydroxyaldehyde promoters corresponding to the unsaturated alcohol or hydroxyaldehyde products desired to be produced and/or higher boiling byproducts as the main protic solvents. Such byproducts can also be preformed if desired and used accordingly. Illustrative preferred protic solvents employable in the production of unsaturated alcohols, e.g., penten-1-ols, or hydroxyaldehydes, e.g., 6-hydroxyhexanal, include alcohols (e.g., pentenols, octanols, hexanediols), amines, thiols, thiophenols, ketones (e.g. acetone and methylethyl ketone), hydroxyaldehydes (e.g., 6-hydroxyaldehyde), lactols (e.g., 2-methylvalerolactol), esters (e.g. ethyl acetate), hydrocarbons (e.g. diphenylmethane, triphenylmethane), nitrohydrocarbons (e.g. nitromethane), 1,4-butanediols and sulfolane. Suitable protic solvents are disclosed in U.S. Pat. No. 5,312,996.

Illustrative substituted and unsubstituted unsaturated alcohol intermediates/starting materials that can be prepared by and/or used in the processes of this invention include one or more of the following: alkenols such as cis-3-penten-1-ol, trans-3-penten-1-ol, 4-penten-1-ol, cis-2-penten-1-ol and/or trans-2-penten-1-ol, including mixtures comprising one or more of the above unsaturated alcohols. The preferred unsaturated alcohols have at least 4 carbon atoms, preferably 4 to about 30 carbon atoms, and more preferably 4 to about 20 carbon atoms.

The hydroformylation stage or step involves the production of hydroxyaldehydes, e.g., 6-hydroxyhexanal, by reacting an olefinic compound salt, e.g., pentenol, with carbon monoxide and hydrogen in the presence of a solubilized metal-ligand complex catalyst and free ligand in a liquid medium that also contains a solvent for the catalyst and ligand. The process may be carried out in a continuous single pass mode in a continuous gas recycle manner or more preferably in a continuous liquid catalyst recycle manner as described above. The hydroformylation processing techniques employable herein may correspond to any known processing techniques such as preferably employed in conventional liquid catalyst recycle hydroformylation reactions. The hydroformylation step or stage may be carried out in a manner similar to that described for the pentenoic acid salt routes above.

The particular amination/hydrogenation and dehydrogenation/cyclization reaction conditions are not narrowly critical and can be any effective amination/hydrogenation and dehydrogenation/cyclization conditions sufficient to produce epsilon caprolactam. The reactors may be stirred tanks, tubular reactors and the like. The exact reaction conditions will be governed by the best compromise between achieving high catalyst selectivity, activity, lifetime and ease of operability, as well as the intrinsic reactivity of the reactants in question and the stability of the reactants and the desired reaction product to the reaction conditions. Products may be recovered after a particular reaction zone and purified if desired although they may be introduced to the next reaction zone without purification. Recovery and purification may be by any appropriate means, which will largely be determined by the particular reactants employed, and may include distillation, phase separation, extraction, absorption, crystallization, derivative formation and the like.

The epsilon caprolactam compositions of this invention prepared by the above pentenol routes comprise epsilon caprolactam and certain byproducts unique to the processes. Illustrative of such byproducts include, for example, one or more of those selected from the group consisting of 5-[4,5-di(4-hydroxybutyl)-2-pyridyl]pentanol, 4-[4,5-di(2-methoxypropyl)-2-pyridyl]-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1-pentanamine, 5-amino-2-methyl-1-pentanol, 5-imino-4-methyl-1-pentanamine and 2-butyl-4,5-dipropylpyridine. These byproducts will typically be present in the final purification steps of the above pentenol routes. Other byproducts that will typically be present in the final purification steps of the above pentenol routes include, for example, one or more of those selected from the group consisting of 5-methyl-2-piperidinone, 4-ethyl-2- pyrrolidinone, 2-butyl-3,5-diisopropylpyridine, 3-ethyl-2-pyrrolidinone, azepane, 3-methylpiperidine, 3-ethylpyrrolidine, 6-aminohexanol, 5-amino-4-methylpentanol, 4-amino-3-ethylbutanol, 6-aminohexanal, 5-amino-4-methylpentanal and 4-amino-3-ethylbutanal. Byproducts that typically will be separated before the final purification steps include, for example, one or more of those selected from the group consisting of 2-oxepanol, 3-methyltetrahydro-2H-2-pyranol, 3-ethyltetrahydro-2-furanol, 1,6-hexanediol, 2-methyl-1,5-pentanediol, 2-ethyl-1,4-butanediol, 3-pentenol and pentanol.

Other byproducts that will typically be present in the epsilon caprolactam compositions derived from the pentenol routes include, for example, one or more of those selected from the group consisting of 4-methyl-5-oxo-1-pentanol, 5-imino-4-methyl-1-pentanol, 5-amino-4-methylpentanal, 3-methyl-2-piperidinone, 3-methylpiperidine, 1,5-diamino-2-methylpentane, 2-methyl-5-oxo-1-pentanol, 5-imino-2-methyl-1-pentanol, 5-amino-2-methylpentanal and 5-methyl-2-piperidinone. Still other byproducts that will typically be present in the epsilon caprolactam compositions derived from the pentenol routes include, for example, one or more of those selected from the group consisting of 3-ethyl-4-oxo-1-butanol, 3-ethyl-4-imino-1-butanol, 4-amino-3-ethyl-1-butanol, 4-amino-3-ethylbutanal, 4-ethyl-2-pyrrolidinone, 3-ethylpyrrolidine, 4-imino-2-ethyl-1-pentanamine, 1,4-diamino-2-ethylpentane, 4-ethyl-2-oxo-1-butanol, 4-imino-2-ethyl-1-butanol, 4-amino-2-ethyl-1-butanol, 4-amino-2-ethylbutanal, 3-ethyl-2-pyrrolidinone, and 4-imino-3-ethyl-1-pentanamine.

An illustrative byproduct is represented by the formula:

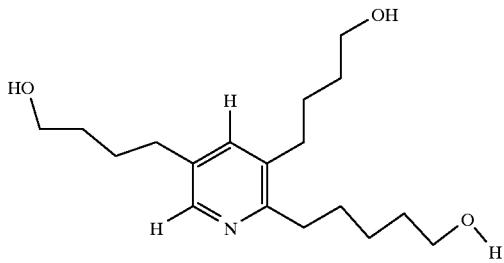

5-[3,5-di(4-hydroxybutyl)-2-pyridyl]pentanol.

As indicated above, it is recognized that byproducts incorporating substituted or unsubstituted linear, branched and/or linear and branched isomers, e.g., pyridines, are included within the scope of this invention.

The amount of epsilon caprolactam and byproducts present in the compositions of this invention can vary over a wide range. Preferably, the weight ratio of epsilon caprolactam to byproducts is at least about 90 to 10, more preferably at least about 99 to 1, and most preferably at least about 99.9 to 0.1.

The processes useful in this invention may be carried out using, for example, a fixed bed reactor, a fluid bed reactor, or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The processes can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones.

The substituted and unsubstituted epsilon caprolactams produced by the processes described herein can undergo further reaction(s) to afford desired derivatives thereof. Such permissible derivatization reactions can be carried out in accordance with conventional procedures known in the art. Illustrative derivatization reactions include, for example, hydrogenation, esterification, polymerization, copolymerization, amination, alkylation, dehydrogenation, reduction, acylation, condensation, oxidation, silylation and the like, including permissible combinations thereof. This invention is not intended to be limited in any manner by the permissible derivatization reactions or permissible derivatives of substituted and unsubstituted epsilon caprolactams.

In an embodiment of this invention, after optional purification of epsilon caprolactam, nylon 6 polymer is produced from epsilon caprolactam by continuous polymerization or batch polymerization processes. In both reaction processes for forming nylon 6, polymerization occurs according to the following reactions: epsilon caprolactam (mol. wt. 113)+$H_2O$→aminocaproic acid (mol. wt. 131)→nylon 6 (mol. wt. 14,000–20,000)+$H_2O$. Suitable reactors and polymerization reaction conditions for nylon 6 are known in the art.

In a continuous polymerization process, high-purity, molten caprolactam is taken from storage and pumped to a tank where controlled amounts of water (the initiator), recovered monomer and oligomers, a chain terminator (e.g., acetic acid) and other additives such as heat and light stabilizers are mixed together. The caprolactam is maintained in a nitrogen environment both in the holding tanks and throughout the polymerization process. The melted caprolactam solution is then filtered and metered into the reaction vessel where polymerization occurs.

The reaction vessel, which is generally eight to ten meters high and mounted vertically, is usually equipped with several independent heating jackets that control the temperature of the reactants as they pass down the tube. Polymerization occurs at atmospheric pressure as the reactants pass slowly through the tube and as the temperature increases to about 275° C. After 20–24 hours, the nylon 6 polymer reaches equilibrium and is extruded as strands into a water quenching bath; the strands are then cut into chips that are also stored under nitrogen.

In a batch polymerization process, high-purity melted epsilon caprolactam (about 80° C.) is pumped into an autoclave. Water, which serves as an initiator, is added to form up to a 5% solution and the temperature of the solution is increased to 220°–270° C. The pressure increases with increasing temperature, and polymerization occurs.

Addition of a polymer chain terminator such as acetic acid controls molecular weight and thus the viscosity of the resin. After several hours, when the caprolactam conversion to polymer has reached equilibrium, water is removed by reducing the pressure to achieve a vacuum. The removal of water is necessary to achieve the desired molecular weight. After the water removal, the polymerization mixture may be held until the molecular weight reaches equilibrium. Finally, the molten resin is extruded as strands into a water quenching bath; the strands are then cut into chips.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

Certain of the following examples are provided to further illustrate this invention.

EXAMPLE 1

A 160 milliliter magnetically stirred autoclave was purged with 1:1 $H_2$/CO and charged with a catalyst solution consisting of 0.1126 grams (0.44 mmol) dicarbonylacetylacetonato rhodium (I), 0.6120 grams (1.69 mmol) P(CH$_2$CH$_2$CH$_2$OH)$_3$, and 39.9 grams of ethanol. The autoclave was pressurized with 40 psig 1:1 $H_2$/CO and heated to 80° C. 6 milliliters (3.73 grams) of 1,3-butadiene was charged with a metering pump and the reactor pressurized to 1000 psig with 1:1 $H_2$/CO. The reaction mixture was maintained at 80° C. under 1000 psi 1:1 $H_2$/CO. Samples of the reaction mixture taken after 15 and 43 minutes provided the following results:

| Time (minutes) | Temperature (° C.) | $H_2$/CO (psig) | Butadiene Conversion (%) | Rate (m/L/h) | Selectivity (%) 3&4 Pentenols |
|---|---|---|---|---|---|
| 15 | 80 | 500/500 | 53 | 2.6 | 70 |
| 43 | 80 | 500/500 | 89 | 1.5 | 78 |

EXAMPLE 2

A 100 milliliter overhead stirred high pressure reactor was charged with 0.10 mmol of dicarbonylacetylacetonato rhodium (I), about 0.20 mmol of 2,2'-(bisdiphenylphosphinomethyl)1,1'-biphenyl, 1 milliliter of 4-pentenol, 26 milliliters of ethanol, and 1 milliliter of diglyme as internal standard. The reactor was pressurized with 5–10 psi of 1/1 hydrogen/carbon monoxide, and heated to 90° C. At 90° C., the reactor was pressurized to 250 psi with 1/1 hydrogen/carbon monoxide at stirred for 1 hour. The reactor gases were vented and the reaction mixture drained and analyzed by gas chromatography. 6-Hydroxyhexanal was formed in 97% selectivity.

EXAMPLE 3

A 100 milliliter Parr autoclave was charged with 0.05 grams of PdCl$_2$ (1000 ppm Pd), and 0.66 grams of Ligand A described below (2 mol ligand per mole palladium). The reactor was sealed and purged with nitrogen, then 25 milliliters of dry 1,4-dioxane, 3 milliliters of butadiene, 1.2 milliliters of water (2 moles per mole butadiene) and 1.08 grams of N-methylpyrrolidinone (as an internal standard) were added via syringe. The reaction mixture was pressurized with 1000 psi carbon monoxide, and heated to 110° C. After 2 hours reaction time, the mixture was analyzed by gas chromatography. Butadiene was 22% converted. The product mixture contained 99.9% of 3-pentenoic acid.

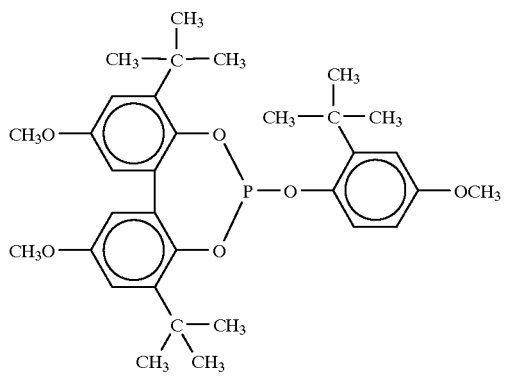

Ligand A

EXAMPLE 4

A 100 milliliter Parr autoclave was charged with 0.10 grams of PdI$_2$ (1000 ppm Pd), and 0.47 grams of Ligand B described below (2 mol ligand per mole palladium). The reactor was sealed and purged with nitrogen, then 25 milliliters of dry 1,4-dioxane, 3 milliliters of butadiene, 1.2 milliliters of water (2 moles per mole butadiene) and 1.08 grams of N-methylpyrrolidinone (as an internal standard) were added via syringe. The reaction mixture was pressurized with 220 psi carbon monoxide and heated to 110° C. After 2 hours reaction time, the mixture was analyzed by gas chromatography. Butadiene was 18% converted. The product mixture contained 99.9% of 3-pentenoic acids.

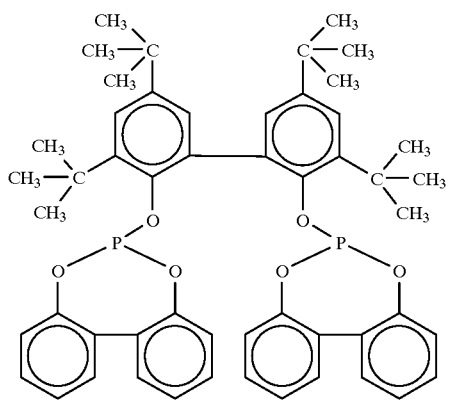

Ligand B

EXAMPLE 5

A 160 milliliter magnetically stirred autoclave was purged with $N_2$ and charged with a catalyst solution consisting of 0.15 mmol of dicarbonylacetylacetonato rhodium (I), 0.73 mmol of Ligand B described above, and 30 milliliters of tetrahydrofuran. The autoclave was pressurized to 10 psig with $N_2$ and heated to 85° C. A solution of the triethylammonium salt of 4-pentenoic acid was prepared by addition of 21 mmol of triethylamine to 22 mmol of 4-pentenoic acid in 4 milliliters of tetrahydrofuran. This solution was added to the autoclave by syringe and the reaction mixture pressurized to 100 psig with 1:1 $H_2$/CO. After 155 minutes of reaction at 85° C., under 100 psi 1:1 H$_2$/CO, gas chromatography analysis of the reaction products (as their free acids) provided the following results: 93% of 5-formylvaleric acid, 3% of branched formylvaleric acids, 4% of valeric acid and <1% of 2-pentenoic acid.

EXAMPLE 6

A 300 milliliter overhead stirred high pressure reactor was charged with 0.30 grams of Cr promoted Raney Ni and placed under an atmosphere of nitrogen. A solution of 0.65 grams of 5-formalvaleric acid in 20 grams of water and 1.2789 grams of diglyme as internal standard was added to the reactor. A sample was taken for gas chromatography analysis, 23.3 grams of 28% NH$_3$ in water was added to the reactor and the reactor pressurized to 700 psi with hydrogen. The reactor was heating to 110° C. at which point the reactor was pressurized to 1000 psi with hydrogen. After one hour, the reactor was cooled and vented to atmospheric pressure. After filtering off the Ni catalyst the resulting solution was charged to a clean 300 milliliter pressure reactor. The reactor was sealed, placed under 50 psi nitroge, and heated to 220° C. After three hours at 220° C., the reactor was cooled, the solution discharged, and a sample was taken for gas chromatography analysis. Analysis of samples taken before and after the reductive amination and cyclization provided the following results by area percent. Caprolactam isomers were not detected in gas chromatographic analysis of the final sample.

|  | Diglyme Area % | 5-Formalvaleric Acid Area % | Epsilon Caprolactam Area % |
| --- | --- | --- | --- |
| Initial GC analysis | 72.0 | 27.9 |  |
| Final GC analysis | 74.6 |  | 25.4 |

EXAMPLE 7

A 160 milliliter magnetically stirred autoclave was purged with 1:1 H$_2$/CO and charged with a solution consisting of 0.7 mmol of Ligand B described above, 5.3 mmol of the triethylammonium salt of 3-pentenoic acid, 2.12 grams diglyme internal standard, and 0.35 grams of tetrahydrofuran. The autoclave was pressurized with 10 psig 1:1 H$_2$/CO and heated to 85° C. A solution of 0.14 mmol of dicarbonylacetylacetonato rhodium (I) in 8.97 grams tetrahydrofuran was added to the reactor, and the reactor maintained at a temperature of 85° C. and a pressure of 100 psig with 1:1 H$_2$/CO for 200 minutes. At this time the reactor was cooled and a sample analyzed by gas chromatography giving the following results for products as their free acids: 67% 5-formylvaleric acid, 5% 4-formylvaleric acid, 3% 3-formylvaleric acid and 25% combined C-5 acids.

A 300 milliliter magnetically stirred autoclave was charged with 1.60 grams of Cr promoted Raney Ni and the reactor placed under an atmosphere of nitrogen. The catalyst solution from the above hydroformylation reaction and 50 milliliters of 28% NH$_3$ in water was charged to the reactor. The reactor was pressurized to 500 psig with hydrogen and heated to 110° C. at which point the pressure was topped off to 990 psig with hydrogen. After one hour, the reactor was cooled and vented to atmospheric pressure. After filtering off the Ni catalyst, the resulting solution was charged to a clean 300 milliliter pressure reactor. The reactor was sealed, placed under 50 psi nitrogen and heated to 220° C. After two hours at 220° C., the reactor was cooled, the solution discharged, and a sample analyzed by gas chromatography giving the following results for products: 71% epsilon caprolactam, 9% 5-methyl-2-piperidinone, 4% 4-ethyl-2-pyrrolidinone, 9% valeric acid and 5% pentanamide.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A composition comprising (a) epsilon caprolactam and (b) one or more of 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-[3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide, 5-[4,5-di(4-hydroxybutyl)-2-pyridyl]pentanol, 4-[4,5-di(2-methoxypropyl)-2-pyridyl]-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1-pentanamine, 5-amino-2-methyl-1-pentanol, 5-imino-4-methyl-1-pentanamine and 2-butyl-4,5-dipropylpyridine, wherein the weight ratio of component (a) to component (b) is at least about 99 to 1.

2. A composition comprising (a) epsilon caprolactam and (b) one or more of 5-[4,5-di(3-carboxypropyl)-2-pyridyl]pentanoic acid or salt or amide, 4-[4,5-di(2-carboxypropyl)-2-pyridyl]-2-methylbutanoic acid or salt or amide, 2-[2-(2-carboxybutyl)-5-(1-carboxypropyl)-4-pyridyl]butanoic acid or salt or amide, 5-[3,5-di(3-carboxypropyl)-2-pyridyl]pentanoic acid or salt or amide, 4-[3,5-di(2-carboxypropyl)-2-pyridyl]-2-methylbutanoic acid or salt or amide, 2-[-2-(2-carboxybutyl)-5-(1-carboxypropyl)-3-pyridyl]butanoic acid or salt or amide, 5-amino-4-methylpentanamide, 4-amino-3-ethylbutanamide and 2-butyl-4,5-dipropylpyridine, wherein the weight ratio of component (a) to component (b) is at least about 99 to 1.

3. A composition comprising (a) epsilon caprolactam and (b) one or more of 5-[4,5-di(4-hydroxybutyl)-2-pyridyl]pentanol, 4-[4,5-di(2-methoxypropyl)-2-pyridyl]-2-methylbutanol, 2-[2-(2-methoxybutyl)-5-(1-methoxypropyl)-4-pyridyl]butanol, 5-[3,5-di(4-hydroxybutyl)-2-pyridyl]pentanol, 4-[3,5-di(2-methoxypropyl)-2-pyridyl]-2-methylbutanol, 2-[2-(2-methoxybutyl)-5-(1-methoxypropyl)-3-pyridyl]butanol, 5-amino-4-methyl-1-pentanol, 5-imino-2-methyl-1-pentanamine, 5-amino-2-methyl-1-pentanol, 5-imino-4-methyl-1-pentanamine and 2-butyl-4,5-dipropylpyridine, wherein the weight ratio of component (a) to component (b) is at least about 99 to 1.

4. The composition of claim 2 further comprising (c) one or more of 5-methyl-2-piperidinone, 4-ethyl-2-pyrrolidinone, 2-butyl-3,5-diisopropylpyridine, 6-aminohexanoic acid or salt or amide, 5-amino-4-methylpentanoic acid or salt or amide and 4-amino-3-ethylbutanoic acid or salt or amide, wherein the weight ratio of component (a) to components (b) and (c) is at least about 99 to 1.

5. The composition of claim 3 further comprising (c) one or more of 5-methyl-2-piperidinone, 4-ethyl-2-pyrrolidinone, 2-butyl-3,5-diisopropylpyridine, 3-methyl-2-piperidinone, 3-ethyl-2-pyrrolidinone, azepane, 3-methylpiperidine, 3-ethylpyrrolidine, 6-aminohexanol, 5-amino-4-methylpentanol, 4-amino-3-ethylbutanol, 6-aminohexanal, 5-amino-4-methylpentanal and 4-amino-3-ethylbutanal, wherein the weight ratio of component (a) to components (b) and (c) is at least about 99 to 1.

6. The composition of claim 4 further comprising (d) one or more of 5-formylvaleric acid, 4-formylvaleric acid, 3-formylvaleric acid, 6-hydroxyhexanoic acid, 5-hydroxy-4-methylpentanoic acid, 3-ethyl-4-hydroxybutanoic acid, 1,3,7-octatriene, 2,7-nonanoic acid, adipic acid, 3-pentenoic acid and pentanoic acid, wherein the weight ratio of component (a) to components (b), (c) and (d) is at least about 99 to 1.

7. The composition of claim 5 further comprising (d) one or more of 2-oxepanol, 3-methyltetrahydro-2H-2-pyranol, 3-ethyltetrahydro-2-furanol, 1,6-hexanediol, 2-methyl-1,5-pentanediol, 2-ethyl-1,4-butanediol, 3-pentenol and pentanol, wherein the weight ratio of component (a) to components (b), (c) and (d) is at least about 99 to 1.

8. The composition of claim 1 in wherein the weight ratio of component (a) to component (b) is at least about 99.9 to 0.1.

9. The composition of claim 1 which is essentially free of cyclohexanol, cyclohexanone, 1-cyclohexanone oxime, 1-cyclohexanamine, phenol, aniline, nitrobenzene, p-toluidine, 1,2,3,4,5,6,7,8,9-octahydrophenazine, adiponitrile, aminocapronitrile, 1-methyl-2-azepanone, 6-(methylamino)hexanoic acid, 6-(methylamino)hexanamide, methyl formylvalerate ester, ethyl formylvalerate ester, propyl formylvalerate ester, methyl 6-hexanoate ester, ethyl 6-hexanoate ester and propyl 6-hexanoate ester.

* * * * *